United States Patent
Spielvogel et al.

(10) Patent No.: US 6,525,224 B1
(45) Date of Patent: Feb. 25, 2003

(54) FUSED POLYHEDRON BORANE DIANION

(75) Inventors: Bernard F. Spielvogel, Fancy Gap, VA (US); Narayan Hosmane, DeKalb, IL (US)

(73) Assignee: Northern Illinois University, DeKalb, IL (US)

( * ) Notice: Subject to any disclaimer, the term of this patent is extended or adjusted under 35 U.S.C. 154(b) by 0 days.

(21) Appl. No.: 09/589,583

(22) Filed: Jun. 7, 2000

Related U.S. Application Data

(60) Provisional application No. 60/138,033, filed on Jun. 8, 1999.

(51) Int. Cl.$^7$ .............................. C07F 5/02; C07F 9/02; A61K 51/00; A61M 36/14
(52) U.S. Cl. .................... 568/5; 568/1; 568/4; 424/1.11
(58) Field of Search ..................... 568/5, 1, 4; 424/1.11

(56) References Cited

U.S. PATENT DOCUMENTS

| | | | | |
|---|---|---|---|---|
| 3,344,108 A | * | 9/1967 | Drinkard | 260/47 |
| 4,824,659 A | * | 4/1989 | Hawthorne | 424/1.1 |
| 5,630,786 A | | 5/1997 | Griffin et al. | |
| 5,648,532 A | | 7/1997 | Hawthrone et al. | |
| 5,679,322 A | * | 10/1997 | Wilbur | 424/9.4 |
| 5,846,741 A | | 12/1998 | Griffiths et al. | |
| 5,976,066 A | | 11/1999 | Yanch et al. | |

OTHER PUBLICATIONS

Volkov, O., Englert, W. Dirk, Paetzold, P., Undecaborates $M_2[B_{11}H_{11}]$: Facile Synthesis, Crystal Structure, and Reactions, Mar. 1999; Abstract.
Barth, R.F., Soloway A.H., and Fairchild, R.G., Cancer Res., 1990, 50, 1061.
Brew, C.T., and Grimes, R.N., J. Am. Chem. Soc., 1984, 106, 2722.
Chao, S., Stalder, C.J., Summers, D.P., and Wrighton, M.S., "Catalysis of the Exchange of Hydrogen and Carbon Isotopes in the Water/Hydrogen and Bicarbonate/Formate Redox Couples: A Comparison of the Exchange Current Densities on the Palladium", J. Am. Chem. Soc. 1984, 106, 2723–2725.
Dunks, G.B., Barker, K., Hedaya, E., Hefner, C., Palmer–Ordonez, K., and Remec, P., Inorg. Chem., 1981, 20, 1692.
Friedman, L.B., Cook, R.E., and Glock, M.D., Inorg. Chem., 1970, 9, 1452.
Friedman, L.B., Cook, R.E., Glick, M.D., "The Crystal and Molecular Structure of Hexadecaborane(20)", Inorg. Chem., vol. 9, No. 6, pp. 1452–1458, Jun. 1970.
Friedman, L.B., Dobrott, R.D., and Lipscomb, W.N., J. Am. Chem. Soc., 1963, 85, 3505.
Greenwood, N.N., In "Comprehensive Inorganic Chemistry", J.C. Bailar, Jr., H.J. Emeleus, R. Nyholm and A. F. T. Dickenson, Eds., 1973, vol. 1, Chapter 11, Ref. 616.
Hatanka, H. and Hakagawa, Y., Int. J. Radiation Oncology Biol. Phys., 1994, 28, 1061.

Hawthorne, M.F., "Boron Hydrides" Chapter 5, pp. 223–323, in "The Chemistry of Boron and Its Compounds", published by John Wilew & Sons, 1967, New York, Earl L. Muetterties, Ed.
Hawthorne, M.F., Angew. Chem. Int. Ed. Engl., 1993, 32, 950.
Hosmane, N.S., Franken, A., Zhang, G., Srivastava, R.R., Smith, R.Y., and Spielvogel, B.F., "Synthesis and Crystal Structure of a Novel Fused Polyhedral Borane Dianion, $[B_{22}H_{22}]^{2-}$: Potential Precursor for Use in Boron Neutron Capture Therapy (BNCT) of Cancer", vol. 21, No. 6, pp. 319–324, 1998.
Hosmane, N.S., Wermer, J.R., Zhu, H., Getman, T.D., and Shore, S.G., Inorg. Chem., 1987, 26, 3638.
Kaczmarczyk, A., Kolski, G.B., and Townsend, W.P., J. Am. Chem. Soc., 1965, 87, 1413.
Middaugh, R.L., In "Boron Hydride Chemistry", E.L. Muetterties, Ed.; Academic Press: New York, N.Y.; 1975, Chapter 8, pp. 273–300.
Moore, E.B., Dickerson, R.E., and Lipscomb, W.N., J. Chem. Phys., 1957, 27, 27.
Sands, D.E., and Zalkin, A., Acta Cryst., 1962, 15, 410.
Sheldrick, G.M., Structure Determination Software Program Package, Siemens Analytical X–ray Instruments, Inc., Madison, WI, USA, 1990.
Simpson, P.G., and Lipscomb, W.N., J. Chem. Phys., 1963, 39, 26.
Simpson, P.G., Folting, K., Dobrott, R.D., and Lipscomb, W.N., J. Chem. Phys., 1963, 39, 2339.
Soloway, A.H., Hatanaka, H., and Davis, M.A., J. Med. Chem., 1967, 10, 714.
Sood, A., Shaw B.R., and Spielvogel, B.F., J. Am. Chem. Soc., 1990, 112, 9000.
Spielvogel, B.F., Sood, A., Shaw A.R., and Hall, I.H., Pure & Appl. Chem., 1991, 63, 415.
Spielvogel, B.F., Sood, A., Shaw, B.R., Hall, I.H., Fairchild, R.G., Laster, B.H., and Gordon, C., In Progress in Neutron Capture Therapy of Cancer, B.J. Allen, et al., Eds.; Plenum Press; New York, N.Y., 1992, 211.
Tippe, A., and Hamilton, W.C., Inorg. Chem., 1969, 8, 464.
Van der Mass Reddy, J. and Lipscomb, W.N., J. Chem. Phys., 1959, 31, 610.
Volkov, O., Dirk, W., Englert, U., Paetzold, P., Z. Anorg. Allg. Chem. 1999, 625, 1193–1201.
Wilson, J.G., Anisuzzaman, A.K.M., Alam, F., and Soloway, A.H., Inorg. Chem., 1992, 31, 1955.
Wunderlich J.A., and Lipscomb, W.N., J. Am. Chem. Soc., 1960, 82, 4427.

* cited by examiner

*Primary Examiner*—Sreeni Padmanabhan
*Assistant Examiner*—Lauren Q. Wells
(74) *Attorney, Agent, or Firm*—Kohn & Associates, PLLC

(57) ABSTRACT

A polyhedral borane cluster consists essentially of a fused polyhedron including an open decaborane cage fused to a closed dodecaborane cluster wherein borane atoms are not an integral part of the cluster vertices. The polyhedral borane cluster can be contained within a biomolecule for use as a neutron capture reagent. A method of synthesizing the polyhedral borane cluster includes the step of fusing an open decaborane cage to a closed dodecaborane cluster.

3 Claims, 2 Drawing Sheets

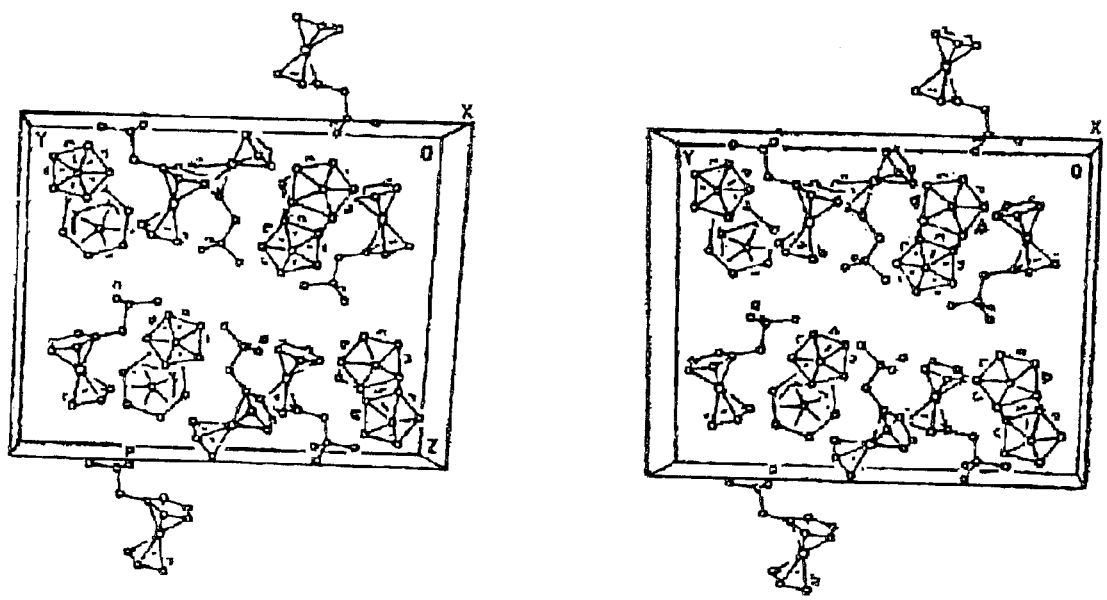
Figure 1. Stereo view of the packing diagram of 1.

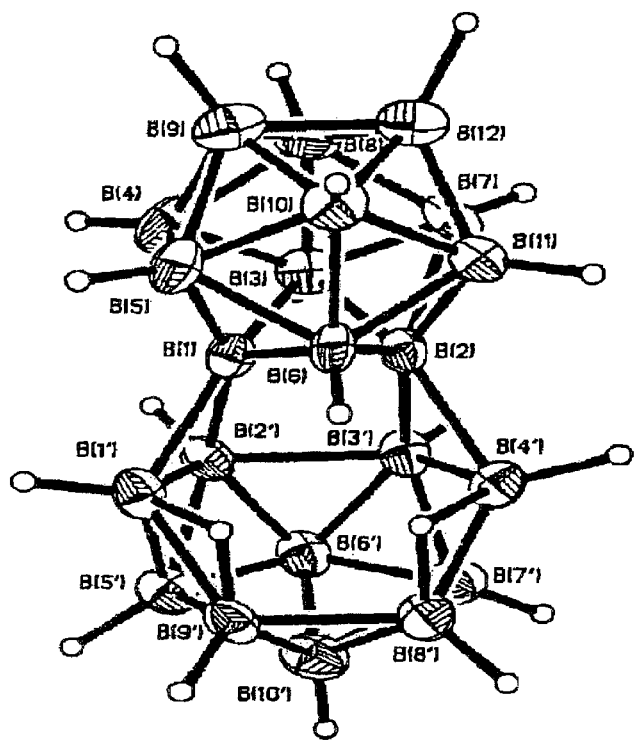
Figure 2. Perspective view of 1 with thermal ellipsoids drawn at the 40% probability level and showing the atom numbering scheme. The $[(\eta^5\text{-}C_5H_5)Fe(\eta^5\text{-}C_5H_4CH_2(Me)_3N)]^+$ cations are omitted for clarity.

FUSED POLYHEDRON BORANE DIANION

CROSS REFERENCE TO RELATED APPLICATIONS

This application claims the benefit of priority of U.S. Provisional Patent Application Serial No. 60/138,033, filed Jun. 8, 1999, and which is incorporated herein by reference.

TECHNICAL FIELD

The present application relates to borane cluster chemistry and the method of making such clusters. More specifically, the present invention relates to borane dianions which are precursors for use in boron, neutron capture therapy of cancer.

BACKGROUND OF THE INVENTION

There has been renewed interest in boron neutron capture therapy of cancer. Neutron capture therapy is an effective therapy for cancer treatment, specifically the treatment of malignant tumors. The method involves capture of a thermalized neutron which is usually from a nuclear reactor with special moderators and ports. This is accomplished by an appropriate nucleus having a large neutron capture cross-section. The subsequent decay emits energetic particles, alpha particles, which kill nearby tumor cells. Since the energetic and cytotoxic alpha particles travel only about one cell diameter in tissue, specificity of the cell type to be destroyed can be obtained by placing the alpha particle precursors only on and within the tumor cells.

Generally, boron neutron capture therapy (BNCT) is based on the nuclear reaction which occurs when a stable isotope, B-10 (present in 19.8% natural abundance) is irradiated with thermal neutrons to produce the alpha particle and a Li-7 nucleus.

Historically, boron neutron capture therapy was first employed for the treatment of glioblastoma (a fatal form of brain tumor) and other brain tumors at a time when tumor specific substances were almost unknown. Problems with previous inorganic boron therapy methods is that the boron reached both targeted and non-targeted areas. Accordingly, when the boron was irradiated, healthy cells as well as cancer cells were destroyed.

More recently, boron neutron capture therapy has been extended to other cancers, spurred on by the discovery of a number of tumor localizing substances, including tumor-targeting monoclonal antibodies.

Considerable activities have recently occurred in the preparation of larger polyhedral boranes and carboranes that have the ability to form a variety of exo-polyhedrally linked biomolecules (1). The importance of synthons to such molecules are the boron-10 enriched neutral decaborane (14), $B_{10}H_{14}$, and the dianionic dodecaborate cluster, $(B_{12}H_{12})^{2-}$. Although both of these compounds can be efficiently synthesized directly from pentaborane (9), $B_5H_9$, that has been stockpiled in U.S. Government inventory (2), the $^{10}B$-enriched species are being prepared by readily available sodium borohydride, $NaBH_4$(3).

The simplified method of Dunks and coworkers for decaborane from sodium borohydride via the $(B_{11}H_{14})^-$ ion has an obvious appeal (4).

Since the decaborane (14) was previously produced only in the optimum yield of 50%, it was speculated that the oxidation step in the procedure could lead to a coupling reaction between two $(B_{11}H_{14})^-$ ions by losing two protons with concomitant page degradation to yield $B_{10}H_{14}$ (4).

Although the oxidation of the $(B_{11}H_{11})^-$ ion in the presence of $FeCl_3$ using anhydrous conditions failed to produce the desired coupled species, $(B_{22}H_{24})^{2-}$ ion, on one occasion the addition of $Me_3NHCl$ to the aqueous mixture of $(B_{11}H_{14})^-$ ion subsequent to its oxidation with hydrogen peroxide yielded a white precipitate. The analytical and spectroscopic data of this white precipitate were consistent with the formula, $(B_{22}H_{24})^{2-}$ in which the $B_{10}$-cage is singly bonded to a $B_{12}$-unit in the $(B_{10}H_{13}-B_{12}H_{11})^{2-}$ cluster (4).

Although such a cluster formation could have resulted from the initial disproportionation reaction of $(B_{11}H_{14})^-$ ion forming 0.5 mole each of $(B_{12}H_{12})^{2-}$ ion and a neutral $B_{10}H_{14}$ followed by the oxidative coupling of these cages, it was clear that more synthetic and structural work was warranted in order to prove this hypothesis. Further work in this area led to the reinvestigation of the work of Dunks and coworkers with a particular interest in establishing reactivity and structural patterns in this large cage.

There has also been investigation into the synthesis and pharmacological properties of boron analogs of biologically important molecules. Many of these molecules are isoelectronic and isostructural with their naturally occurring carbon counterparts. Based upon 4-coordinate boron, these molecules generally possess sufficient hydrolytic and oxidative stability to be used in biological studies. They can be used to probe fundamental biochemical events at the molecular level as well as providing entirely new classes of compounds for potential medical value. These compounds also prove valuable in boron neutron capture therapy. For example, potential biological activity has been found for various of these new species, such as boronated nucleosides and nucleotides (3C). Amino acid analogs have ranged from simple glycine and N-methyl substituted glycines to analogs of more complex amino acids, such as alanine. Other amides of common amino acids have likewise been prepared and these derivatives as well as many other related precursors and derivatives of simple glycines including peptides are now commercially available (3C).

It is desirable to establish reactivity and structural patterns in large cage systems. Such systems are envisioned to be precursors for selected biomolecules that can be used in boron neutron capture therapy of cancer.

SUMMARY OF THE INVENTION

In accordance with the present invention there is provided a polyhedral borane cluster consisting of a fused polyhedron including an open (nido) decaborane cage fused to a closed (closo) dodecaborane cluster wherein borane atoms are not integral parts of the cluster vertices. The present invention also provides a method for synthesizing a polyhedral borane cluster by fusing an open (nido) decaborane cage to a closed (closo) dodecaborane cluster. Also, the present invention provides a neutron capture reagent consisting essentially of the polyhedral borane cluster including the open decaborane cage fused to the closed dodecaborane cluster, the polyhedral borane cluster being conjugated to a biomolecule.

BRIEF DESCRIPTION OF THE DRAWINGS

Other advantages of the present invention will be readily appreciated as the same becomes better understood by reference to the following detailed description when consider in connection with the accompanying drawings wherein:

FIG. 1 is a stereo view of the packing diagram of the polyhedral borane cluster of the present invention; and FIG. 2 is a perspective view of the polyhedral borane cluster of the present invention with thermal ellipsoids drawn at the 40% probability level and showing the atom numbering schemes.

DETAILED DESCRIPTION OF THE INVENTION

Most generally, the present invention provides a polyhedral borane cluster and method of making the same.

Borane is one of the series of boron hydrides (compounds of boron and hydrogen). The simplest of these, $BH_3$ is unstable at atmospheric pressure and becomes diborane ($B_2H_6$), a gas at normal pressures. This is usually converted to higher boranes penta-, deca-, etc. by condensation. The series progresses through a number of well characterized crystals and compounds. It is common knowledge to those skilled in the art of chemistry that hydrides exist up to $B_{20}H_{26}$. Most are not very stable and readily react with water to yield hydrogen and many react violently with the air. As a rule, these compounds are highly toxic. Due to their reactivity, their properties have suggested investigation for rocket propulsion, but they have not proved to be satisfactory for that purpose. There are also a number of organoboranes used as reducing agents and so called electroless nickel-plating of metals and plastics. Some of the compounds used are di- and tri-ethylamine borane and pyridine borane.

In accordance with the present invention, a polyhedral borane anion $(B_{22}H_{22})^{2-}$ was synthesized and its crystalline structure characterized as a novel fused polyhedral borane dianion whose $^{10}B$-enriched species is a precursor for selected biomolecules that can be used in boron neutron capture therapy of cancer. The $(B_{22}H_{22})^{2-}$ species and its derivatives can also be incorporated into liposomes and microspheres and the like for use in BNCT.

The polyhedral borane cluster consists essentially of a fused polyhedron including an open (nido) decaborane cage fused to a closed (closo) dodecaborane cluster wherein the boron atoms are not integral parts of the cluster vertices. The polyhedral skeleton form can be accurately described as deltahedra (all faces triangular) or deltahedral fragments. In their regular form, all of these idealized structures are convex deltahedra except for the octadecahedron, which is not a regular polyhedron. These compounds fall into a class of deltahedral closo molecules from which all other idealized structures can be generated systematically. The nido or arachno cluster can be generated from the appropriate deltahedron by ascending a diagonal from left to right. This progression generates the nido structure by removing the most highly connected vertex of the deltahedron and the arachno structure is formed by removal of the most highly connective atom of the open face of the nido cluster.

These terms closo, nido and arachno as well as hypho implies closed, nest-like, web-like and net-like structures, respectively. In addition to boranes, these classifications apply to heteroboranes and their metallo analogs and are intimately connected to a quality called the framework electron count. The partitioning of electrons into exopolyhedral and framework classes allows the accurate prediction of structure in most cases, even though the systematics are not concerned explicitly with the assignment of localized bonds within the skeleton.

Nido and arachno boranes are generally much more reactive and thermally less stable than closo boranes. Closo boranes contain some very stable molecules that make their chemistry atypical among the boranes. These molecules have been characterized to constitute a series of $(B_nH_n)^{2-}$ ($n=6-12$) delta hedral anions. Unlike their nido and arachno counterparts with bridge hydrogens, for practical purposes, the abstraction of the hydrogen ion does not occur in closo borane chemistry. Instead, acid catalysis plays an important role in their substitution chemistry.

Consistent with the present invention, the preferred formula is:

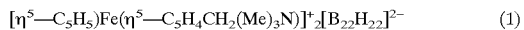

$$[\eta^5-C_5H_5)Fe(\eta^5-C_5H_4CH_2(Me)_3N)]^+_2[B_{22}H_{22}]^{2-} \quad (1)$$

The preferred compound (1) was synthesized by the following procedure.

In a slightly modified procedure, described by Dunks and coworkers (4) for the preparation of $B_{10}H_{14}$, the room temperature reaction between the tetramethylethylenediamine-solvated sodium undecaborate, $\{[Na(TMEDA)_2][B_{11}H_{14}]^-\}$, and hydrogen peroxide in 1:9 stoichiometry in 1:1:1 solvent mixture of benzene, hexane and water in the presence of aqueous sulfuric acid, followed by the cation exchange with ferrocenylmethyl-N,N,N-trimethylammonium iodide and subsequent crystallization from aqueous acetonitrile solution produced the novel fuxed polyhedral borane cluster, identified as $\{[\eta^5-C_5H_5)Fe(\eta^5-C_5H_4CH_2(Me)_3N)]^+_2[B_{22}H_{22}]^{2-}\}$ (1), in 60% yield. It will be appreciated by one skilled in the art that variations in the amounts of reactants and ratio of solvents can be accommodated and at least some of the $(B_{22}H_{22})^{2-}$ species obtained. Other cations cmmonly used to precipitate polyhedral boron hydride anions such as alhylammonium, phosphonium, arsonium, $CS^+$ can also be used to afford precipitates of $(B_{22}H_{22})^{2-}$. This procedure is set forth in detail in the Experiments and Examples section set forth below. Other oxidative coupling procedures can be used to prepare $(B_{22}H_{22})^{2-}$. For example, see Paetzold et al.

Although the exact mechanism for the formation of (1) is not known, a plausible sequence of reactions, shown in equation (1) can be deduced from the experimental conditions used in the synthesis. Since it has been established that $[B_{11}H_{14}]^-$ cage can be either expanded to $[B_{12}H_{12}]^{2-}$ by reacting with

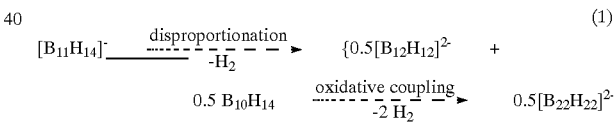

(1)

one equivalent of $NaBH_4$ [5] or degraded to $B_{10}H_{14}$ by oxidation with a variety of oxidizing agents [4], it is possible that the $[B_{11}H_{14}]^-$ ion can initially undergo a disproportionation reaction when treated with sulfuric acid before its further oxidative coupling reaction with $H_2O_2$ as shown in equation (1). However, unlike $[B_{12}H_{12}]^{2-}$ ion which is relatively unstable under chemical oxidizing conditions decomposing to boric acid [6], 1 is unexpectedly found to be a stable species which do not seem to undergo ready degradation to form $B_{10}H_{14}$ or some other product(s) under the vigorous experimental conditions used in its preparation (see Experimental Examples).

It is of interest to note that the reaction between $Na[B_{11}H_{14}]\cdot 2.5$ dioxane and $HgBr_2$ in THF led to the conjuncto-dianion $[B_{22}H_{26}]^{2-}$ which, on the basis of its IR and NMR spectra, was thought to have the structure of two $B_{11}$ cages linked by a direct B—B bond at the apical position [7].

The $^1H$ and $^{13}C$ NMR spectra indicated the rpesence of the ferrocenylmethyl-N,N,N-trimethylammonium unit in 1, in addition to showing the rpesence of bridging hydrogens in the $^1H$ NMR spectrum. However, the proton-coupled $^{11}B$ NMR spectrum exhibited a down-field singlet at δ8.71 ppm, with other up-field doublets at δ−13.05, −16.9, −19.1, and −22.2 and −32.2 ppm in roughly 1:2:3:2:2:1 peak area ratio. Only the resonances at δ8.71 (singlet) and δ32.2 ppm (doublet) were separated enough that the δs have significance with the former being assigned to the fused borons and the other for the apical borons. With the exception of peak area ratios, the $^{11}$B NMR spectra of 1 is almost identical to those observed by Dunks and coworkers for the white precipitate obtained during the oxidation of $[B_{11}H_{14}]$ ion in aqueous medium (4). Nonetheless, the set of resonances centered near δ17 ppm, could not be assigned ambiguously. Moreover, the solution IR spectrum does not reveal any additional information about the cage geometry other than simply exhibiting the presence of ferrocenylmethyl-N,N,N-trimethylammonium moiety, the terminal BH units and the bridging (B—H—B) hydrogens. Therefore, the unambiguous geometry of the title compound was determined by X-ray diffraction studies. This constitutes the first structural report on a fused polyhedral borane cluster containing more than 20 cage atoms without the metals being integral part of the cluster vertices.

The crystal packing diagram (FIG. 1) shows that compound 1 consists of two $\{[\{\eta^5—C_5H_5\}Fe(\eta^5—C_5H_4CH_2(Me)_3N)]^+$ cations with no appreciable contact with the dianionic cluster, $[B_{22}H_{22}]^{2-}$, indicating that there is no significant interaction between them.

The structure of the anionic unit in 1, shown in FIG. 2, is a fused polyhedron in which a slightly distorted icosahedral $B_{12}H_{10}$-cage is fused with an open $B_{10}H_{12}$ unit involving two of the lower belt basal boron atoms in the former cage and four of the upper belt borons in the latter unit with concomitant elimination of the two terminal and two bridging hydrogens respectively. Thus, 1 is structurally related to several other borane polyhedra having 12–20 boron atoms, in which two borane cages share a common edge. Among them $B_{12}H_{16}$ [8], $B_{16}H_{20}$[9], $B_{18}H_{22}$[10], i-$B_{18}H_{22}$[11], and $B_{20}H_{16}$[12] cluster geometries are noteworthy. The open $B_{10}H_{12}$ unit contains two B—H—B bridges [H(1'9') and H(4'8')] which are in close proximity of B(1) and B(2) atoms that share the common edge without the terminal H's. Consequently, the resonances in the $^{11}$B NMR spectra are broad due to some degree of cage functionality on the NMR time scale.

The B—B distances of 1.740(13)–1.838(12) Å in the $B_{12}H_{10}$ unit of 1 are comparable, but not identical, to those found in the discrete $[B_{12}H_{12}]^{2-}$ ion cluster of $I_h$ symmetry [13]. The distortion of the cage arises from the longer distances of the B(1) and B(2) atoms to the atoms of the fused adjacent $B_{10}H_{12}$ cage; these distances are B(1)–B(1')= 1.929(13) Å, B(1)–B(2')=1.977(13) Å, B(2)–B(3')=1.981(13) Å and B(2)–B(4')=1.930(13) Å (see FIG. 2 and Table 1). On the other hand, the B—B distance sin the $B_{10}H_{12}$ unit are in the range of 1.736(12)–1.797(14) Å except for the predictably large value of 1.846(13), 1.870(13), 1.920(14) and 2.090(13) Å for the corresponding B(4')–B(8'), B(1')–B(9'), B(8')–B(9') and B(2')–B(3') bonds where bridging H's were originally present as in the structure of the parent decaborane (14), $B_{10}H_{14}$ [14]. Within the allowed errors of estimation, the geometry of the $B_{10}H_{12}$ unit in 1 is identical to those determined for a number of $L_2B_{10}H_{12}$ adducts [15,16]. The geometries of the $[(\eta^5—C_5H_5)Fe(\eta^5—C_5H_4CH_2(Me)_3N)]^+$ cationic units are unexceptional (see Table 1) and deserve no special comment.

The hydride of the dodecaborane can be substituted with a member from the group including halogen, amines, thio groups, amide, alkyl, CO, $N_2$, COOR, OH, OR, and many others as shown in M. F. Hawthorn, "Boron Hydride", Chapter 5. Likewise, a hydride of the decaborane can be substituted with a member from the group including halogens, amines, thiogroups, amides, alkyl, OH, OR, as shown in M. F. Hawthorne, "Boron Hydrides", Chapter 5. Multiple substitutions can also be made of hydrides from the same substituent groups.

The substitution of the hydrides in either the dodecaborane or the decaborane can be accomplished by the following method.

The two fused cages in the $B_{22}H_{22}$ dianion are closely related to the icosahedral $B_{12}H_{12}$ dianion and the doubly bridged structure of decaborane as described above. Thus, the chemistry of this species can be developed along the lines of these two species which has been extensively explored. For reference, see M. F. Hawthorne, "Boron Hydrides" Chapter 5, pages 223–323, in "The Chemistry of Boron and Its Compounds" published by John Wilew & Sons, 1967, New York, Earl L. Muetterties, Ed.

The chemistry of decaborane is very versatile and examples of its reactivity include:

(a) proton abstraction to form anionic species;
(b) electrophilic substitution of hydrogen to form halogenated, alkylated, etc., derivatives;
(c) electron transfer reactions to form anionic species;
(d) reactions with ligands such as nitrites, sulfides, amines, and others to form $B_{10}H_{12}$(ligand)2 derivatives;
(e) reactions of $B_{10}H_{10}$(ligand)2 species with acetylenes to form carboranes;
(f) transistion metal derivatives of the various hydride and carborane derivatives.

Other examples may be found in the above reference. Carborane derivatives will be among the most valuable and versatile species.

The chemistry of $B_{12}H_{12}$ dianion has been extensively explored and examples of its derivatives include substitution of hydrogen by halogens, sulfur, amines, hydroxy, alkyl and many others.

Thus, the uniqueness of the $B_{22}H_{22}$ dianion lies in its hybrid character of two very important and extensively explored boron hydride species, the icosahedral $B_{12}H_{12}$ dianion and decaborane. The derivative chemistry should be vast and of great use to many applications of boron hydrides to medical and industrial use.

The present invention further provides a neutron capture reagent consisting essentially of the polyhedral borane cluster of the present invention contained within a biomolecule. The biomolecule can be selected from the group including nucleosides, oligonucleotides, oligonucleosides, amino acids, amino acid analogs, peptides and polypeptides, steroids, carbohydrates, phospholipids, and many others as already described in the literature on BNCT. The neutron capture reagent prepared under the present invention can also be attached to tumor seeking compounds such as porphrins, diamines or other synthetic tumor seeking compounds. The neutron capture reagent can also be encapsulated into a tumor seeking liposome or encapsulated into a tumor seeking liposome or encapsulated into microspheres and microspheres attached to tumor seeking species. Amino acid analogs and boronated nucleosides and nucleotides and their synthesis applicable to the present invention is disclosed by Spielvogel et al. (3C). Amino acid analogs have ranged from simple glycine and N-methyl substituted glycines to analogs of more complex amino acids such as analine (amide). Other amides of common amino acids can likewise be prepared and these derivatives, as well as many other related precursors and derivatives of simple glycines including peptides are now commercially available. A variety of potent pharmacological activity has been expressed by these amino acid analogs such as hypolipidemic anti-cancer, and anti-inflammatory activity.

The synthesis of new classes of nucleic acid components has been stimulated by anti-viral and anti-tumor activity associated with a wide variety of structurally divergent modified nucleic acids. In addition to therapeutic potential, modified nucleosides, mononucleotides, and oligonucleotides have been shown usefulness as diagnostic agents and as probes for setting fundamental biological processes at the molecular level. Boronated nucleic acids have added importance to localize in the nucleus and prove very effective in boron neutron capture therapy of cancer. Specifically designed boronated oligonucleotides can also function as antisense molecules and inhibit or completely block expression of oncogenes.

For use in boron neutron capture therapy, a high concentration of boron is specifically localized at the tumor sites by pretargeting the tumor sites with a tumor antigen selective monoclonal antibody conjugated to one member of the cluster, such as aviden or streptaviden. The antibody used selectively binds the antigens produced by or associated with tumor cells. The use of a selective monoclonal antibody is inherently more specific, however, the cluster can be bound to other tumor specific directing biomolecules, such as proteins, amino acids, peptide fragments or the like. Likewise, there is a desire to target the boron neutron capture therapy to the nucleus. For this purpose, the cluster is coupled to a nucleoside, nucleotide or the like, which can be a sense or antisense form.

Antibody fragments useful in the present invention include F(ab')$_2$, F(ab)$_2$, F(ab)', F(ab), and other hybrid fragments. Also useful are any subfragments containing or retaining the hyper variable antigen binding region of the immunoglobulin and having a similar size to or smaller than an F(ab)' fragment.

Routes of administration of such compositions used in the present invention include intravenous, intraarterial, intrapleural, intraperitoneal, intrathecal, subcutaneous or by profusion. The timing of such administration can be optimized to enhance the efficiency of boron delivery. The time of maximum tumor uptake of the complex conjugate can be determined by various methods known in the pharmacological art.

Treatment is accomplished by administering the cluster made in accordance with the present invention conjugated to a targeting agent to a cancer patient and allowing the conjugate to localize at the tumor site. After localization, there is subsequent tissue irradiation with thermal neutrons. Boron is non-radioactive until a thermal neutron is captured, causing the known fission reaction. The resulting alpha and lithium particles are high in energy and travel less than 10 microns in tissue as discussed above. The tissue is thereby ablated. Depending on the ligand conjugated to the cluster, ablation can occur at the tumor membrane or nucleus.

The following examples provide a factual basis for the method of synthesis and utility of the present invention.

EXPERIMENTAL EXAMPLES

Synthesis of 1: In a slightly modified procedure described elsewhere [4], A 12 mmol (4.66 g) sample of {[Na(TMEDA)$_2$][B$_{11}$H$_{14}$]$^-$}, was suspended in 50 mL of 1:1:1 solvent mixture of benzene, hexane and water. To this mixture at room temperature, 13 mL of sulfuric acid (65% v/v) was added cautiously with constant stirring. At this point, a solution of hydrogen peroxide (13 g, 30%, 114.7 mmol) was slowly added to the above stirred reaction mixture over a period of one hour at room temperature. After stirring for six days at room temperature, the organic and aqueous layers of the mixture were separated by conventional method using a separating funnel. The removal of solvents from the organic layer resulted in the isolation of 0.23 g (1.88 mmol, 16% yield) of B$_{10}$H$_{14}$. To the filtered aqueuos layer 4.62 g (12 mmol) of [($\eta^5$—C$_5$H$_5$)Fe($\eta^5$—C$_5$H$_4$CH$_2$(Me)$_3$N)]I in 1:1 mixture of THF/H$_2$O ws added which resulted in a yellow precipitate and was isolated by filtration. This yellow solid was recrystallized from aqueous acetonitrile solution to collect {[($\eta^5$—C$_5$H$_5$)Fe($\eta^5$—C$_5$H$_4$CH$_2$(Me)$_3$N)]$^+_2$[B$_{22}$H$_{22}$]$^{2-}$} (1), in 60% yield (2.79 g, 3.59 mmol; m.p. >250° C.).

Analytical and Spectroscopic Data of 1: Anal. Calcd for C$_{28}$H$_{62}$B$_2$N$_2$Fe$_2$: C, 43.32; H, 8.05; N, 3.61. Found: C, 43.39; H, 8.16; Cl, 3.56. $^1$H NMR (THF-d$_8$, external Me$_4$Si) δ3.78 [x, 8H, C$_5$H$_4$], 3.65 [s, 10H, C$_5$H$_5$], 2.97 [s, 4H, CH$_2$], 2.11 [s (br), 18H, Me], −2.36 [s (v br), 2H, B—H—B bridge]; $^{11}$B NMR (THF-d$_8$, external BF$_3$ Oet$_2$) δ8.71 [s (br), 2B, basal borons sharing a common edge], −13.05 [d(br, overlapping), 4B, basal BH, $^1$J($^{11}$B—$^1$H)= unresolved], −19.1 [br, ill-defined peak, 4B, basal BH, $^1$J($^{11}$B—$^1$H)=unresolved], −32.2 [d(br), 2B, apical BH, $^1$J($^{11}$B—$^1$H)=135 Hz]; $^{13}$C NMR (THF-d$_8$, external Me$_4$Si) δ72.15 [s, ferrocenyl carbon], 69.87 [d, C$_5$H$_4$, $^1$J($^{13}$C—$^1$H)= 176 Hz], 69.02 [d, C$_5$H$_5$, $^1$J($^{13}$C—$^1$H)=177 Hz], 47.44 [t, CH$_2$, $^1$J($^{13}$C—$^1$H)=144 Hz], 41.83 [q (br), Me, $^1$J($^{13}$C—$^1$H)=140 Hz]; IR (cm$^{-1}$; THF vs. THF): 3099 (s, s) [v(C—N)], 2950 (vs), 2926 (vs), 2891 (s, s, [v(C—H)], 2580 (vs), 2558 (vs) [v(B-h)], 2396 (w, s), 2297 (m, s), 1917 (w, br) [v(B—H—B)], 1768 (s, s), 1717 (m, s), 1655 (w, br), 1516 (s, s), 1450 (s, s), 1412 (s, s), 1350 (m, s), 1258 (vs), 1210 (m), (w, s), 2297 (m, s), 1917 (w, br) [v(B—H—B)], 1768 (s, s), 1717 (m, s), 1655 (w, br), 1516 (s, s), 1450 (s, s), 1412 (s, s), 1350 (m, s), 1258 (vs), 1210 (m), 1073 (s, s), 907 (s, s), 840 (vs), 805 (sh), 750 (vs), 636 (w, s), 595 (m, s), 485 (m, s).

X-ray Analysis of 1: C$_{28}$H$_{62}$B$_{22}$N$_2$Fe$_2$, fw=776.3, monoclinic, P2$_1$/c, a=10.727 (5), b=21.674 (7), c=18.558 (8) Å, β=103.16 (3), V-4201 (3) Å$^3$, Z=4, $^D$calcd=1.227 g/cm$^3$, $\mu$=0.715 mm$^{-1}$. Of 7800 data collected on a Siemens R3mN diffractometer (MoKα, 2θ=3.0–50.0°, at 299 K) 7340 reflections were unique and 3460 reflections were observed [F>6.0σ(F)]. Data were corrected for Lorenz, polarization, and absorption (based on ψ scans) effects. The structure was solved by Direct methods and refined by full-matrix least-squares techniques using SHELXTL-Plus [17]. All non-H atoms were refined anisotropically. Cage-H atoms were located in difference Fourier maps, and methyl and methylene H atoms were calculated using a riding model. The final refinement of 1 converged at R=0.0482, wR=0.0525, and GOF=2.48 for observed reflections.

TABLE 1

SELECTED BOND LENGTHS (Å) AND BOND ANGLES (°) FOR 1

BOND LENGTHS

| | | | | | |
|---|---|---|---|---|---|
| Fe(1)-C(11) | 2.028 (7) | C(111)-N(1) | 1.519 (9) | B(2)-B(4') | 1.930 (13) |
| Fe(1)-C(12) | 2.039 (8) | C(112)-N(1) | 1.503 (10) | B(3)-B(4) | 1.801 (15) |
| Fe(1)-C(13) | 2.052 (9) | C(113)-N(1) | 1.510 (11) | B(3)-B(7) | 1.760 (14) |
| Fe(1)-C(14) | 2.053 (8) | C(114)-N(1) | 1.499 (11) | B(3)-B(8) | 1.734 (16) |
| Fe(1)-C(15) | 2.031 (7) | C(21)-C(22) | 1.436 (11) | B(4)-B(5) | 1.787 (12) |
| Fe(1)-C(16) | 2.042 (10) | C(21)-C(25) | 1.423 (9) | B(4)-B(8) | 1.803 (17) |
| Fe(1)-C(17) | 2.045 (9) | C(21)-C(211) | 1.489 (10) | B(4)-B(9) | 1.787 (15) |
| Fe(1)-C(18) | 2.025 (8) | C(22)-C(23) | 1.404 (11) | B(5)-B(6) | 1.792 (13) |
| Fe(1)-C(19) | 2.028 (9) | C(23)-C(24) | 1.420 (12) | B(5)-B(9) | 1.772 (15) |
| Fe(1)-C(110) | 2.037 (10) | C(24)-C(25) | 1.419 (12) | B(5)-B(10) | 1.792 (14) |
| Fe(2)-C(21) | 2.024 (7) | C(26)-C(27) | 1.401 (17) | B(6)-B(10) | 1.740 (13) |
| Fe(2)-C(22) | 2.039 (7) | C(26)-C(210) | 1.361 (20) | B(6)-B(11) | 1.777 (13) |
| Fe(2)-C(23) | 2.063 (9) | C(27)-C(28) | 1.370 (17) | B(7)-B(8) | 1.792 (15) |
| Fe(2)-C(24) | 2.066 (9) | C(28)-C(29) | 1.419 (17) | B(7)-B(11) | 1.776 (11) |
| Fe(2)-C(25) | 2.030 (8) | C(29)-C(210) | 1.340 (16) | B(7)-B(12) | 1.789 (15) |
| Fe(2)-C(26) | 2.029 (12) | C(211)-N(2) | 1.532 (9) | B(8)-B(9) | 1.783 (16) |
| Fe(2)-C(27) | 2.045 (11) | C(212)-N(2) | 1.503 (10) | B(8)-B(12) | 1.769 (14) |
| Fe(2)-C(28) | 2.014 (10) | C(213)-N(2) | 1.501 (9) | B(9)-B(10) | 1.748 (12) |
| Fe(2)-C(29) | 2.026 (14) | C(214)-N(2) | 1.476 (10) | B(9)-B(12) | 1.804 (16) |
| Fe(2)-C(210) | 2.033 (12) | B(1)-B(2) | 1.757 (1.2) | B(10)-B(11) | 1.789 (14) |
| C(11)-C(12) | 1.447 (9) | B(1)-B(3) | 1.838 (1.2) | B(10)-B(12) | 1.765 (13) |
| C(11)-C(15) | 1.439 (10) | B(1)-B(4) | 1.794 (12) | B(11)-B(12) | 1.773 (14) |
| C(11)-C(111) | 1.482 (10) | B(1)-B(5) | 1.806 (13) | B(1')-B(2') | 1.736 (12) |
| C(12)-C(13) | 1.407 (12) | B(1)-B(6) | 1.773 (10) | B(1')-B(5') | 1.739 (14) |
| C(13)-C(14) | 1.418 (10) | B(1)-B(1') | 1.929 (13) | B(1')-B(9') | 1.870 (13) |
| C(14)-C(15) | 1.415 (11) | B(1)-B(2') | 1.977 (13) | B(2')-B(3') | 2.090 (13) |
| C(16)-C(17) | 1.415 (13) | B(2)-B(3) | 1.801 (12) | B(2')-B(5') | 1.767 (14) |
| C(16)-C(110) | 1.395 (14) | B(2)-B(6) | 1.785 (11) | B(2')-B(6') | 1.754 (15) |
| C(17)-C(18) | 1.419 (15) | B(2)-B(7) | 1.769 (13) | B(3')-B(4') | 1.747 (11) |
| C(18)-C(19) | 1.433 (12) | B(2)-B(11) | 1.803 (12) | B(3')-B(6') | 1.750 (14) |
| C(19)-C(110) | 1.393 (13) | B(2)-B(3') | 1.981 (13) | B(3')-B(7') | 1.760 (14) |
| B(4')-B(7') | 1.743 (15) | B(5')-B(10') | 1.753 (14) | B(7')-B(10') | 1.771 (15) |
| B(4')-B(8') | 1.846 (13) | B(6')-B(7') | 1.786 (14) | B(8')-B(9') | 1.920 (14) |
| B(5')-B(6') | 1.797 (14) | B(6')-B(10') | 1.773 (13) | B(8')-B(10') | 1.782 (14) |
| B(5')-B(9') | 1.793 (12) | B(7')-B(8') | 1.779 (13) | B(9')-B(10') | 1.750 (15) |

BOND ANGLES

| | | | |
|---|---|---|---|
| B(2)-B(1)-B(3) | 60.1 (5) | B(5)-B(1)-B(1') | 108.9 (6) |
| B(2)-B(1)-B(4) | 108.5 (7) | B(6)-B(1)-B(1') | 103.9 (5) |
| B(3)-B(1)-B(4) | 59.4 (5) | B(2)-B(1)-B(2') | 94.6 (6) |
| B(2)-B(1)-B(5) | 109.6 (6) | B(3)-B(1)-B(2') | 88.0 (5) |
| B(3)-B(1)-B(5) | 107.2 (6) | B(4)-B(1)-B(2') | 117.3 (5) |
| B(4)-B(1)-B(5) | 59.5 (5) | B(5)-B(1)-B(2') | 155.4 (7) |
| B(2)-B(1)-B(6) | 60.7 (5) | B(6)-B(1)-B(2') | 134.5 (6) |
| B(3)-B(1)-B(6) | 107.1 (6) | B(1')-B(1)-B(2') | 52.8 (4) |
| B(4)-B(1)-B(6) | 107.1 (6) | B(1)-B(2)-B(3) | 62.2 (5) |
| B(5)-B(1)-B(6) | 60.1 (5) | B(1)-B(2)-B(6) | 60.1 (5) |
| B(2)-B(1)-B(1') | 119.2 (6) | B(3)-B(2)-B(6) | 108.2 (6) |
| B(3)-B(1)-B(1') | 140.7 (6) | B(1)-B(2)-B(7) | 109.6 (6) |
| B(4)-B(1)-B(1') | 131.4 (7) | B(3)-B(2)-B(7) | 59.1 (5) |

Based on the above experimental examples, the presence of two B—H—B bridging hydrogens along the dinegative charge on the cluster suggest that the preferred compound (1) can undergo further reactions leading to selective cage functionalities as discussed above. The results are the synthesis of a number of biomolecules containing the fused $B_{22}$ cluster. The above results indicate that (1) is a stable cluster which can be synthesized from $^{10}$B-enriched $NaBH_4$ in a reasonable yield. These results of the reactivity study suggest that the functionalized compounds that have a high probability of preferentially localizing and tumors rather than normal tissues can be synthesized from (1) and can be used in boron neutron capture therapy of cancer. The above experimental examples also demonstrate a number of novel fused clusters of borane and carborane systems that can be synthesized and their activity patterns established.

REFERENCES 1. (a) M. F. Hawthorne, Angew. Chem. Int. Ed. Engl., 1993, 32, 950. (b) H. Hatanka and Y. Hakagawa, Int. J. Radiation Oncology Biol. Phys., 1994, 28, 1061. (c) A. H. Soloway, H, Hatanaka and M. A. Davis, J. Med. Chem., 1967, 10, 714. (d) R. F. Barth, A. H. Soloway and R. G. Fairchild, Cancer Res., 1990, 50, 1061. (e) J. G. Wilson, A. K. M. Anisuzzaman, F. Alam and A. H. Soloway, Inorg. Chem., 1992, 31, 1955.
2. N. S. Hosmane, J. R. Wermer, H. Zhu, T. D. Getman and S. G. Shore, Inorg. Chem., 1987, 26, 3638.
3. (a) B. F. Spielvogel, A. Sood, B. R. Shaw, I. H. Hall, R. G. Fairchild, B. H. Laster and C. Gordon, In Progress in Neutron Capture Therapy of Cancer, B. J. Allen, et al., Eds.; Plenum Press; New York, N.Y., 1992, 211. (b) A. Sood, B. R. Shaw and B. F. Spielvogel, J. Am. Chem. Soc., 1990, 112, 9000. (c). B. F. Spielvogel, A. Sood, B. R. Shaw and I. H. Hall, Pure & Appl. Chem., 1991, 63, 415.
4. G. B. Dunks, K. Barker, E. Hedaya, C. Hefner, K. Palmer-Ordonez and P. Remec, Inorg. Chem., 1981, 20, 1692.

5. R. L. Middaugh, In "Boron Hydride Chemistry", E. L. Muetterties, Ed.; Academic Press: New York, N.Y.; 1975, Chapter 8, pp. 273–300.
6. A. Kaczmarczyk, G. B. Kolski and W. P. Townsend, J. Am. Chem. Soc., 1965, 87, 1413.
7. N. N. Greenwood, In "Comprehensive Inorganic Chemistry", J. C. Bailar, Jr., H. J. Emeleus, R. Nyholm and A. F. T. Dickenson, Eds., 1973, Vol. 1, Chapter 11, Ref. 616.
8. C. T. Brewer and R. N. Grimes, J. Am. Chem. Soc., 1984, 106, 2722.
9. L. B. Friedman, R. E. Cook and M. D. Glock, Inorg. Chem., 1970, 9, 1452.
10. P. G. Simpson and W. N. Lipscomb, J. Chem. Phys., 1963, 39, 26.
11. P. G. Simpson, K. Folting, R. D. Dobrott and W. N. Lipscomb, J. Chem. Phys., 1963, 39, 2339.
12. L. B. Friedman, R. D. Dobrott and W. N. Lipscomb, J. Am. Chem. Soc., 1963, 85, 3505.
13. J. A. Wunderlich and W. N. Lipscomb, J. Am. Chem. Soc., 1960, 82, 4427.
14. (a) E. B. Moore, R. E. Dickerson and W. N. Lipscomb, J. Chem. Phys., 1957, 27, 27. (b) A. Tippe and W. C. Hamilton, Inorg. Chem., 1969, 8, 464.
15. J. Van der Mass Reddy and W. N. Lipscomb, J. Chem. Phys., 1959, 31, 610.
16. D. E. Sands and A. Zalkin, Acta Cryst., 1962, 15, 410.
17. G. M. Sheldrick, Structure Determination Software Program Package, Siemens Analytical X-ray Instruments, Inc., Madison, Wis., USA, 1990.
18. M. F. Hawthorne, "Boron Hydrides" Chapter 5, pages 223–323, in "The Chemistry of Boron and Its Compounds", published by John Wilew & Sons, 1967, New York, Earl L. Muetterties, Ed.

What is claimed is:

1. A polyhedral borane cluster consisting essentially of:
a fused polyhedron including an open (nido) decaborane cage fused to a closed (closo) decaborane cluster, wherein borane atoms are not on the cluster vertices, wherein the polyhedral cluster is $$[(\eta^5-C_5H_5)Fe(\eta^5-C_5H_4CH_2(Me)_3N)]^+{}_2[B_{22}H_{22}]^{2-}.$$

2. A polyhedral borane cluster as in claim 1 consisting of two $[(\eta^5-C_5H_5)Fe(\eta^5-C_5H_4CH_2(Me)_3N)]^+$ cations independent of constant contact with the dianionic cluster $[B_{22}H_{22}]^{2-}$.

3. A polyhedral borane cluster as in claim 1 wherein said polyhedral borane cluster consists of a $B_{12}H_{10}$ cluster fused with an open $B_{10}H_{12}$ cage involving two lower belt basal boron atoms in said cage and four upper belt boron atoms in said cluster wherein two bridging and two terminal hydrogens are eliminated whereby said cage and cluster share a common edge.

* * * * *